United States Patent [19]

Lemanski et al.

[11] Patent Number: 5,304,678
[45] Date of Patent: Apr. 19, 1994

[54] ACETIC ACID FROM ETHYLENE

[75] Inventors: Michael F. Lemanski, Hull, Great Britain; Joseph B. Hazen, Garfield Heights; Patricia R. Blum, Macedonia, both of Ohio

[73] Assignee: The Standard Oil Company, Cleveland, Ohio

[21] Appl. No.: 625,191

[22] Filed: Dec. 10, 1990

[51] Int. Cl.⁵ .................... B01J 27/185; C07C 51/16
[52] U.S. Cl. ..................................... 562/548; 502/213
[58] Field of Search ...................... 502/213; 562/548

[56] References Cited

U.S. PATENT DOCUMENTS

| | | | |
|---|---|---|---|
| 3,104,263 | 9/1963 | Riemenschneider | 562/548 |
| 3,534,093 | 10/1970 | Gerberich et al. | 562/548 |
| 3,574,730 | 4/1971 | Capp et al. | 562/548 |
| 3,792,087 | 2/1974 | McClain et al. | 562/548 |

*Primary Examiner*—José G. Dees
*Assistant Examiner*—Joseph M. Conrad, III
*Attorney, Agent, or Firm*—Charles S. Lynch; Michael F. Esposito; David J. Untener

[57] ABSTRACT

Disclosed is making acetic acid by reacting in a reaction zone ethylene and molecular oxygen in the presence of a solid catalyst containing the elements and proportions indicated by the empirical formula $$Pd_a M_b TiP_c O_x \quad \text{(formula 1)}$$

where
M is selected from Cd, Au, Zn, Tl, alkali metals and alkaline earth metals,
a is from 0.0005 to 0.2
b is from zero to 3a
c is 0.5 to 2.5, and
x is a value sufficient to satisfy the valence requirements of the other elements present, and wherein such catalyst contains crystalline $TiP_2O_7$.

16 Claims, No Drawings

ACETIC ACID FROM ETHYLENE

The present invention relates to a catalyst useful for the oxidation of ethylene to acetic acid, as well as to the process for such oxidation using such catalyst.

It is an object of the present invention to provide a novel and superior supported palladium metal catalyst for the production of acetic acid by the oxidation of ethylene with molecular oxygen.

Another object of the invention is to provide a novel process for the oxidation of ethylene to acetic acid using such catalyst.

Other objects, as well as aspects, features and advantages, of the present invention will become apparent from a consideration of the specification, including the specific examples and the claims.

These and other objects are achieved by the present invention, wherein according to one aspect thereof there is provided a process for making acetic acid which comprises reacting in a reaction zone ethylene and molecular oxygen in the presence of a solid catalyst containing the elements and proportions indicated by the empirical formula $$Pd_aM_bTiP_cO_x \qquad \text{(formula 1)}$$

where
M is selected from Cd, Au, Zn, Tl, alkali metals and alkaline earth metals,
a is from 0.0005 to 0.2
b is from zero to 3a
c is 0.5 to 2.5, and
x is a value sufficient to satisfy the valence requirements of the other elements present, and
wherein such catalyst contains crystalline $TiP_2O_7$.

In the above formula 1, a is usually from 0.005 to 0.05 more usually from 0.002 to 0.04; and c is usually not less than 0.8 nor more than 2, more often not over 1.25.

When M is used, b is usually at least 0.0001a.

We have found that the crystalline $TiP_2O_7$, titanium pyrophosphate, is not only an effective and mechanically tough physical support for the palladium component of the catalyst, but also contributes to the catalytic activity. Thus, a catalyst made with Pd, $H_3PO_4$ and $SiO_2$ as a support, as in U.S. Pat. No. 3,792,087 gives less than half the yield of acetic acid from ethylene and oxygen, compared to a catalyst of the present invention. Note examples 27 and Comparative Examples C.6 and C.7 herein.

In another aspect of the invention there is provided a process for oxidizing ethylene with molecular oxygen in the presence of a catalyst defined above.

The reaction of oxygen and ethylene to make acetic acid does not require the introduction of water into the reaction zone, although the reaction produces some water by the unwanted combustion of some of the ethylene. As a practical matter we usually introduce some water into the reaction zone along with the ethylene and oxygen, since it appears to promote the conversion of ethylene to acetic acid. Many of the specific examples include added water in the feed.

The oxygen in the feed to the reaction zone can be pure oxygen gas or, alternatively, an oxygen-containing gas mixture such as air or air enriched with oxygen. In addition to these materials the gaseous feed mixture reacted in the process can contain other diluents such as carbon dioxide, nitrogen or acetic acid, as well as reactive diluents such as acetaldehyde.

The ethylene feed to the reaction zone can be substantially pure or, alternatively, can be impure in the sense that it may contain even large amounts such as 90 mol % or more $C_1$ to $C_3$ saturated hydrocarbon gases or vapors as diluents.

The following specific examples are illustrative only and are not to be taken as limiting. The empirical formula of each catalyst is shown at the beginning of each example. The catalyst examples of the invention contain crystalline $TiP_2O_7$, titanium pyrophosphate.

In making the catalysts of the invention, it is necessary to heat or calcine the composition sufficiently to result in the formation of the necessary $TiP_2O_7$ crystalline phase. This is not accomplished at calcination temperatures up to 200° C. It is accomplished in those specific examples of the invention which are calcined at temperatures of 400° to 850° C. What is not known is the lowest temperature at which $TiP_2O_7$ can be formed below 400° C. and above 200° C., but this can easily be checked by routine trial and error by calcining at various temperatures at various times and then subjecting the resulting calcined composition to X-ray powder diffraction testing to detect the presence of the crystalline compound sought.

COMPARATIVE EXAMPLE 1: 2 wt % Pd/15 wt % $H_3PO_4/SiO_2$ 2.6 g of $Pd(NO_3)_2$ was dissolved in 100 ml of distilled water. 9.2 g of 85% phosphoric acid and 122.3 g of Nalco 1034A silica sol (34 wt % $SiO_2$) was added. The mixture was refluxed for one hour then evaporated to a thick paste. The solid was dried at 110° C. overnight, ground and screened. The portion which passed through 20 mesh but was retained on the 35 mesh screen was calcined at 400° C. for 16 hours.

COMPARATIVE EXAMPLE 2: wt % Pd/44% $H_3PO_4/SiO_2$

The procedure was the same as used in comparative example 1, except that 27.0 g of phosphoric acid and 82.3 g of silica sol were used.

EXAMPLE 1: $TiPd_{0.03}PO_x$

Palladium acetate $[Pd(OOCCH_3)_2]_3$ (3.71 g) was added to 200 ml of distilled water. This slurry was heated with stirring at about 60°–80° C. for 30 minutes. By the end of this time the slurry was dark brown and a portion of the palladium acetate had dissolved. To this slurry was added 57.8 g of 85% phosphoric acid, followed by the addition of 40.0 g of titanium dioxide. This slurry was then boiled and dried down to a thick paste. This paste was placed in a drying oven at about 110° C., and dried overnight. After drying the solid was ground and screened. The through 20 on 35 mesh portion was calcined in air at 400° C. for 20 hours.

COMPARATIVE EXAMPLE 3: $TiPd_{0.03}PO_x$

Palladium acetate (9.276 g) was slurried in 500 ml of distilled water and heated the slurry for 30 min at ~80° C. Phosphoric acid (85% $H_3PO_4$, 144.5 g) was added to the slurry followed by 100 g of titanium dioxide. The mixture was evaporated to a thick paste then dried in the oven (~110° C., air) overnight. The solid was ground and screened to pass through 10 mesh and be retained on 35 mesh. No calcination was performed.

EXAMPLE 2: $TiPd_{0.03}PO_x$

Palladium acetate (11.13 g) was slurried in 500 ml of distilled water and heated the slurry for 30 min at ~80° C. Phosphoric acid (85% $H_3PO_4$, 173.4 g) was added to the slurry followed by 120 g of titanium dioxide. The mixture was evaporated to a thick paste then dried in the oven (~110° C., air) overnight. The solid was broken into pieces, and calcined for 16 hrs at 400° C. The final solid was ground and screened to pass through 20 mesh and be retained on 35 mesh.

EXAMPLE 3: $TiPd_{0.03}PO_x$

A portion of Example 2 was calcined for an additional 16 hrs at 600° C.

EXAMPLE 4: $TiPd_{0.03}PO_x$

A portion of Example 2 was calcined for an additional 16 hrs at 800° C.

COMPARATIVE EXAMPLE 4: $TiPd_{0.03}PO_x$

A portion of Example 2 was calcined for an additional 16 hrs at 1000° C.

EXAMPLE 5: $TiPd_{0.04}P_{1.33}O_x$

The reagents: 3.71 g of palladium acetate, 57.8 g of 85% phosphoric acid, and 30.0 g titanium dioxide were combined as described in Example 1. However this sample was calcined in air for 16 hrs at 400° C.

EXAMPLE 6: $TiPd_{0.03}PO_x$

The procedure was the same as with Example 5 except 40.0 g of titanium dioxide were used.

EXAMPLE 7: $TiPd_{0.024}P_{0.8}O_x$

The procedure was the same as with Example 5 except 50.0 g of titanium dioxide were used.

EXAMPLE 8: $TiPd_{0.02}P_{0.67}O_x$

The procedure was the same as with Example 5 except 60.0 g of titanium dioxide were used.

EXAMPLE 9: $TiPd_{0.075}PO_x$

In 150 ml of distilled water, 11.58 g of palladium nitrate, 57.8 g of 85% phosphoric acid and 40 g of titanium dioxide were combined. The slurry was evaporated to a thick paste with high heat. The paste was dried overnight at 110° C., ground and screened, and the 20/35 mesh portion was calcined at 400° C., under air for 16 hours.

EXAMPLE 10: $TiPd_{0.05}P_{0.98}O_x$

The procedure was the same as in Example 9 except 6.19 g of palladium 5 acetate, 56.6 g of 85% phosphoric acid, and 40.0 g of titanium dioxide were used.

EXAMPLE 11: $TiPd_{0.04}PO_x$

The procedure was the same as in Example 9 except 4.95 g of palladium acetate, 57.2 g of 85% phosphoric acid, and 40.0 g of titanium dioxide were used.

EXAMPLE 12: $TiPd_{0.03}PO_x$

The procedure was the same as in Example 9 except 3.71 g of palladium acetate, 57.8 g of 85% phosphoric acid, and 40.0 g of titanium dioxide were used.

EXAMPLE 13: $TiPd_{0.02}P_{1.01}O_x$

The procedure was the same as in Example 9 except 2.47 g of palladium acetate, 58.4 g of 85% phosphoric acid, and 40.0 g of titanium dioxide were used.

EXAMPLE 14: $TiPd_{0.01}P_{1.02}O_x$

The procedure was the same as in Example 9 except 1.24 g of palladium acetate, 59.0 g of 85% phosphoric acid, and 40.0 g of titanium dioxide were used.

EXAMPLE 15: $TiPd_{0.03}PO_x$

Palladium acetate (3.71 g) was added to 200 ml of distilled water. This slurry was heated with stirring at about 60°–80° C. for 30 minutes. By the end of this time the slurry was dark brown and a portion of the palladium acetate had dissolved. To this slurry was added 57.8 g of 85% $H_3PO_4$, followed by the addition of 40.0 g of titanium dioxide. This slurry was then boiled and dried down to a thick paste. This paste was placed in a drying oven set at ~110° C., and dried overnight. The solid was then broken into small pieces and calcined in air at 800° C. for 16 hours. After calcination the solid was ground to 20/35 mesh particle size range.

EXAMPLE 16: $TiPd_{0.003}PO_x$

The following reagents: 0.3345 g of palladium acetate, 52.0 g of 85% phosphoric acid, and 36.0 g of titanium dioxide were added to 200 ml of distilled water. The mixture was heated at 70° C. for 30 minutes. The heat was then increased and the slurry was evaporated to a thick paste. The paste was dried overnight at 200° C., ground and screened, and the 20/35 mesh portion of the solid was calcined at 700° C., in air for 16 hours.

EXAMPLE 17: $TiPd_{0.03}PO_x$

Palladium acetate (3.714 g) was dissolved in 200 ml of glacial acetic acid which was heated to ~80° C. for 30 min. Phosphoric acid (85% $H_3PO_4$, 57.81 g) was added to the solution followed by the titanium dioxide (40.0 g). Using high heat (hot plate) the slurry was evaporated to a thick paste. This paste was dried at ~110° C. in air overnight. The solid was then ground and screened to 10/35 mesh particles and calcined for 8 hrs at 800° C.

EXAMPLE 18: $TiPd_{0.03}K_{0.07}PO_x$

Palladium acetate (2.23 g) was added to 120 ml of distilled water. This slurry was heated with stirring at about 60°–80° C. for 5 minutes. Then 2.07 g of potassium nitrate was added to the slurry and the heating was continued for 30 minutes. By the end of this time the slurry was dark brown and a portion of the palladium acetate had dissolved. To this slurry was added 34.7 g of 85% $H_3PO_4$, followed by the addition of 24.0 g of titanium dioxide. This slurry was then boiled and dried down to a thick paste. This paste was placed in a drying oven set at ~110° C., and dried overnight. The solid was then broken into pieces and calcined in air at 800° C. for 8 hours. After calcination the solid was ground to 10/35 mesh particle size range.

EXAMPLE 19: $TiPd_{0.01}K_{0.03}PO_x$

Palladium acetate (1.114 g) was added to 200 ml of distilled water. This slurry was heated with stirring at about 60°–80° C. for 5 minutes. Then 1.33 g of potassium nitrate was added to the slurry and the heating was continued for 30 minutes. By the end of this time the slurry was dark brown and a portion of the palladium acetate had dissolved. To this slurry was added 52.0 g of 85% $H_3PO_4$, followed by the addition of 36.0 g of titanium dioxide. This slurry was then boiled and dried down to a thick paste. This paste was placed in a drying oven set at 200° C., and dried overnight. The solid was then ground and screened; the 20/35 mesh portion of the solid was calcined in air at 700° C. for 16 hours.

EXAMPLE 20: $TiPd_{0.03}K_{0.07}Cd_{0.03}PO_x$

The procedure was the same as in Example 18 except that immediately after the addition of potassium nitrate, 1.80 g of cadmium acetate was added to the slurry.

EXAMPLE 21: $TiPd_{0.03}Ca_{0.07}PO_x$

Palladium acetate (3.71 g) and calcium nitrate $XH_2O$ (6.58 g) were added to 200 ml of distilled water. This slurry was heated with stirring at about 60°-80° C. for 30 minutes. To this slurry was added 57.8 g of 85% $H_3PO_4$, followed by the addition of 40.0 g of titanium dioxide. This slurry was then boiled and dried down to a thick paste. This paste was placed in a drying oven set at 200° C., and dried overnight. The solid was then ground and screened to produce a 10/35 mesh portion. This 10/35 mesh portion was calcined in air at 800° C. for 16 hours.

EXAMPLE 22: $TiPd_{0.03}Na_{0.12}PO_x$

The procedure was the same as in example 21 except 5.05 g of sodium 15 nitrate was used instead of the calcium nitrate.

EXAMPLE 23: $TiPd_{0.03}Ca_{0.007}PO_x$

The procedure was the same as example 21, except that 2.23 g of palladium acetate, 120 ml of distilled water, 0.396 g of calcium nitrate hydrate, 34.7 g of 85% phosphoric acid and 24.0 g of titanium dioxide were used. Calcination was carried out in air for 16 hours at 700° C.

EXAMPLE 24: $TiPd_{0.03}Ca_{0.0007}PO_x$

The procedure was the same as example 21 except that 0.039 g of calcium nitrate hydrate were used. Calcination was carried out in air for 16 hrs at 700° C.

COMPARATIVE EXAMPLE 5: $TiPO_x$

To 200 ml of distilled water which was heated to 60°-80° C., was added 57.8 g of 85% phosphoric acid followed by 40.0 g of titanium dioxide. This slurry was evaporated on high heat (hot plate) to a thick paste. Sample was dried in air at 110° C. Sample was ground and screened to 10/35 mesh sized particles, calcined in air for 16 hrs at 790° C. After calcination a 20/35 mesh particle size range fraction was screened from the sample.

The conditions for the synthesis runs to make acetic acid are summarized in the following tables. These oxidation runs were carried out in a stainless steel tubular reactor containing a fixed bed of the designated particulate catalyst. The reactor was equipped with a central thermowell within which a thermocouple could be variably positioned in order to probe the temperature of the catalyst bed under reaction conditions. The reactor was fitted into an electrically heated, suitcase-type furnace. Gaseous feeds to the reactor were controlled by electronic mass flow controllers; liquid feeds were pumped to the reactor using a Waters Model 590 liquid chromatograph pump. They were vaporized prior to contacting the catalyst bed. Feeds were passed through the reactor in the downflow configuration. Reactor pressure was controlled with a Tescom back pressure regulator.

Catalyst was tested in the form of particles ground to size, 0.35-1.68 mm in diameter (the fraction which passed through 10 mesh but not 40 mesh). The reactor effluent was passed through a distilled water scrubber which was chilled with ice in order to dissolve all liquid products. The remaining gaseous stream was analyzed by gas chromatography for ethylene, ethane, methane, oxygen, nitrogen, carbon monoxide and carbon dioxide content. The liquid scrubber sample was analyzed for acetaldehyde, ethanol, ethylacetate, vinylacetate, and acetic acid using a cross-linked methyl silicone capillary column in a Hewlett-Packard gas chromatograph. Acetic acid was also quantitated via titration using a Brinkman 665 Dosimat and 686 Titroprocessor.

While the particular temperatures and pressures are not the essence of the invention, it should be noted that zero to 400 psig and up to and above 250° C. (560° C. in one control example) were used. These examples serve as a guide to one skilled in the art. For instance, as the temperature, and especially as the pressure, is raised, it becomes increasingly difficult to control the exotherm, to the point that a runaway reaction can occur. In that event the addition of a moderator element M, or the lowering the concentration of Pd in the catalyst composition or both, generally tends to allow the use of higher reaction zone operating pressures while avoiding an uncontrollable reaction zone temperature increase.

As will be evident to those skilled in the art, various modifications of this invention can be made or followed in the light of the foregoing disclosure and discussion without departing from the spirit and scope of the disclosure or from the scope of the claims.

TABLE 1

| Oxidation Example No. | Catalyst Example No. | CT Secs | Pressure psig | Temperature °C. | Feed Mol ratios $C_2=/O_2/N_2/H_2O$ | Percent $C_2=$ Conv. | $CH_3COOH$ Yield Based on $C_2=$ |
|---|---|---|---|---|---|---|---|
| 25 | 19 | 21 | 180 | 205 | 1/1.76/14.1/3.9 | 100 | 72.8 |
| 26 | 19 | 12 | 100 | 183 | Same as Above | 66.4 | 50.4 |
| C. 6 | C. 1 | 1.45 | 0 | 200 | 1/1.85/13.5/3.2 | 39.7 | 26.6 |
| C. 7 | C. 2 | 1.35 | 0 | 200 | 1/1.92/15.3/3.3 | 27.8 | 16.9 |
| 27 | 1 | 1.41 | 0 | 201 | 1/1.95/13.6/3.1 | 83.5 | 55.3 |
| C. 8 | C. 3 | 1.46 | 0 | 200 | 1/1.85/14.4/3.9 | 5.4 | 2.2 |
| 28 | 2 | 1.46 | 0 | 200 | 1/1.85/13.8/3.4 | 62.2 | 42.9 |
| 29 | 3 | 1.37 | 0 | 200 | 1/1.85/13.8/3.2 | 65.9 | 45.8 |
| 30 | 4 | 1.47 | 0 | 200 | 1/1.85/13.8/3.3 | 67.8 | 51.1 |
| C. 9 | C. 4 | 1.42 | 0 | 200 | 1/1.85/13.8/3.2 | 7.3 | 1.4 |
| 31 | 1 | 1.42 | 0 | 200 | 1/1.96/17.3/2.3 | 74.7 | 44.4 |
| 32 | 1 | 1.37 | 0 | 200 | 1/1.95/15.9/3.3 | 76.5 | 47.1 |
| 33 | 1 | 1.36 | 0 | 200 | 1/1.91/12.5/5.3 | 74.2 | 40.3 |

TABLE 1-continued

| Oxidation Example No. | Catalyst Example No. | CT Secs | Pressure psig | Temperature °C. | Feed Mol ratios $C_2=/O_2/N_2/H_2O$ | Percent $C_2=$ Conv. | $CH_3COOH$ Yield Based on $C_2=$ |
|---|---|---|---|---|---|---|---|
| C. 10 | C. 5 | 6.4 | 47 | 203 | 1/1.88/13.9/4.0 | 0 | 0 |
| C. 11 | C. 5 | 3.8 | 50 | 560 | 1/1.90/14.1/4.0 | 62.5 | 0 |
| 34 | 5 | 1.42 | 0 | 200 | 1/1.90/14.2/3.2 | 61.6 | 41.0 |
| 35 | 6 | 1.37 | 0 | 200 | 1/1.90/13.6/3.0 | 79.4 | 50.3 |
| 36 | 7 | 1.36 | 0 | 200 | 1/1.90/13.6/3.0 | 66.1 | 39.5 |
| 37 | 8 | 1.36 | 0 | 200 | 1/1.90/13.6/3.0 | 58.8 | 36.9 |
| 38 | 9 | 1.42 | 0 | 206 | 1/1.87/13.6/3.1 | 93.4 | 56.0 |
| 39 | 10 | 1.38 | 0 | 200 | 1/1.93/14.5/3.2 | 87.7 | 58.0 |
| 40 | 11 | 1.40 | 0 | 200 | 1/1.93/14.4/3.2 | 83.2 | 54.4 |
| 41 | 12 | 1.30 | 0 | 200 | 1/1.91/15.5/3.2 | 80.0 | 49.6 |
| 42 | 13 | 1.40 | 0 | 200 | 1/1.95/14.4/3.2 | 71.1 | 47.4 |
| 43 | 14 | 4.5 | 30 | 197 | 1/1.87/14.4/3.9 | 52.3 | 34.0 |
| 44 | 15 | 4.6 | 30 | 189 | 1/1.88/14.2/3.9 | 69.0 | 52.0 |
| 45 | 15 |  | 50 | runaway exotherm |  |  |  |
| 46 | 16 | 67 | 400 | 201 | 1/1.79/14.1/3.9 | 59.6 | 36.1 |
| 47 | 17 | 2.4 | 0 | 200 | 1/1.88/6.1/4.0 | 69.5 | 52.4 |
| 48 | 18 | 10 | 80 | 192 | 1/1.87/14.2/3.9 | 82.3 | 58.5 |
| 49 | 20 | 45 | 400 | 184 | 1/1.77/14.2/3.9 | 76.4 | 54.3 |
| 50 | 21 | 43 | 400 | 204 | 1/1.76/14.0/3.8 | 86.0 | 54.7 |
| 51 | 23 | 16 | 90 | 177 | 1/1.90/12.8/5.8 | 67.6 | 38.5 |
| 52 | 24 | 7.1 | 50 | 163 | 1/1.85/14.4/4.0 | 56.4 | 40.7 |
| 53 | 24 |  | When P of Run 52 was increaaed to 90 psig a runaway exotherm occurred. |  |  |  |  |

$C_2=$ means ethylene.
"C" means "Comparative".
CT means Contact Time.

We claim:

1. A process for making acetic acid which comprises reacting in a reaction zone ethylene and molecular oxygen in the presence of a solid catalyst containing the elements and proportions indicated by the empirical formula $$Pd_aM_bTiP_cO_x \qquad \text{(formula 1)}$$

where
M is selected from Cd, Au, Zn, Tl, alkali metals and alkaline earth metals,
a is from 0.0005 to 0.2
b is from zero to 3a
c is 0.5 to 2.5, and
x is a value sufficient to satisfy the valence requirements of the other elements present, and
wherein said catalyst contains crystalline $TiP_2O_7$.

2. A process of claim 1 wherein a is from 0.005 to 0.05.
3. A process of claim 1 wherein c is not over 2.
4. A process of claim 1 wherein c is not less than 0.8.
5. A process of claim 1 wherein c is in the range from 0.8 to 2.
6. A process of claim 2 wherein c is not over 2.
7. A process of claim 2 wherein c is not less than 0.8.
8. A process of claim 2 wherein c is in the range from 0.8 to 2.
9. A solid catalyst containing the elements and proportions indicated by the empirical formula $$Pd_aM_bTiP_cO_x \qquad \text{(formula 1)}$$

where
M is selected from Cd, Au, Zn, Tl, alkali metals and alkaline earth metals,
a is from 0.0005 to 0.2
b is from zero to 3a
c is 0.5 to 2.5, and
x is a value sufficient to satisfy the valence requirements of the other elements present, and
wherein said catalyst contains crystalline $TiP_2O_7$.

10. A catalyst of claim 9 wherein a is from 0.0005 to 0.05.
11. A catalyst of claim 9 wherein c is not over 2.
12. A catalyst of claim 9 wherein c is not less than 0.8.
13. A catalyst of claim 9 wherein c is in the range from 0.8 to 2.
14. A catalyst of claim 10 wherein c is not over 2.
15. A catalyst of claim 10 wherein c is not less than 0.8.
16. A catalyst of claim 10 wherein c is in the range from 0.8 to 2.

* * * * *

UNITED STATES PATENT AND TRADEMARK OFFICE
CERTIFICATE OF CORRECTION

PATENT NO. : 5,304,678
DATED : April 19, 1994
INVENTOR(S) : Michael F. Lemanski et al.

It is certified that error appears in the above-identified patent and that said Letters Patent is hereby corrected as shown below:

Claim 10, column 8, line 43, change "0.0005" to --0.005--.

Signed and Sealed this

First Day of November, 1994

Attest:

BRUCE LEHMAN

Attesting Officer        Commissioner of Patents and Trademarks